(12) United States Patent
Donaty

(10) Patent No.: US 8,240,213 B2
(45) Date of Patent: Aug. 14, 2012

(54) SYSTEM AND METHOD FOR ULTRASONIC SAMPLE PREPARATION

(75) Inventor: Michael Donaty, Danbury, CT (US)

(73) Assignee: Sonics & Materials Inc, Newtown, CT (US)

( * ) Notice: Subject to any disclaimer, the term of this patent is extended or adjusted under 35 U.S.C. 154(b) by 471 days.

(21) Appl. No.: 12/239,183

(22) Filed: Sep. 26, 2008

(65) Prior Publication Data

US 2009/0151459 A1    Jun. 18, 2009

Related U.S. Application Data

(60) Provisional application No. 60/975,645, filed on Sep. 27, 2007.

(51) Int. Cl.
*G01M 7/00* (2006.01)
*G01N 1/00* (2006.01)

(52) U.S. Cl. ............... 73/662; 73/64.56; 73/863

(58) Field of Classification Search ............. 73/64.56, 73/23.41, 61.59, 662, 863.01; 366/109, 110
See application file for complete search history.

(56) References Cited

U.S. PATENT DOCUMENTS

| | | | | |
|---|---|---|---|---|
| 3,100,987 A | * | 8/1963 | Bincer | 73/641 |
| 3,269,172 A | * | 8/1966 | McGaughey | 324/71.4 |
| RE30,926 E | * | 5/1982 | Ross et al. | 73/638 |
| 4,914,966 A | * | 4/1990 | White et al. | 73/863.01 |
| 4,930,898 A | * | 6/1990 | Miller-Ihli | 366/109 |
| 5,693,228 A | * | 12/1997 | Koehler et al. | 210/656 |
| 5,736,100 A | * | 4/1998 | Miyake et al. | 422/64 |
| 6,318,158 B1 | * | 11/2001 | Breen et al. | 73/64.56 |
| 6,393,893 B1 | * | 5/2002 | Fetz et al. | 73/19.01 |
| 6,492,184 B1 | * | 12/2002 | Petro et al. | 506/5 |
| 2005/0031499 A1 | * | 2/2005 | Meier | 422/128 |

* cited by examiner

*Primary Examiner* — J M Saint Surin
(74) *Attorney, Agent, or Firm* — St. Onge Steward Johnston & Reens LLC

(57) ABSTRACT

A system for ultrasonic sample preparation includes a sample container having a wall defining an outer surface and an inner volume for containing a sample material, a converter which converts AC electricity to mechanical vibrations in the ultrasonic range, and an ultrasonic probe in contact with the outer surface of the sample container. The ultrasonic probe is in communication with the converter and transmits the mechanical vibrations in the ultrasonic range to the wall of the sample container and thereby to the inner volume, thereby mixing the sample material.

13 Claims, 2 Drawing Sheets

SYSTEM AND METHOD FOR ULTRASONIC SAMPLE PREPARATION

CROSS-REFERENCE TO RELATED APPLICATIONS

The present application claims the benefit under 35 U.S.C. §119 (e) of the U.S. Provisional Patent Application Ser. No. 60/975,645 filed on Sep. 27, 2007.

FIELD OF THE INVENTION

The present invention relates to the use of ultrasonic energy to process materials. In particular, the present invention relates to a system and method for mixing sample materials using ultrasonic energy.

BACKGROUND OF THE INVENTION

It is well known to use ultrasonic energy to prepare sample materials for diagnostic investigation. When analyzing a sample material, particularly a sample consisting of two or more materials, it is important that the sample be as homogeneously mixed as possible. Such thorough and complete mixing tends to provide more consistent and accurate diagnostics of the sample.

Ultrasonic energy is used to provide complete and homogeneous mixing of liquid samples. This is generally accomplished by inserting a probe, generally made of a metal such as titanium, into a sample vessel containing the material sample and then vibrating the probe at an ultrasonic frequency. Such vibration, typically between 20 kHz and 40 kHz, causes "cavitation" to occur in the liquid sample. Cavitation refers to the rapid formation and collapse of vapor pockets in a liquid in regions of very low pressure. In the case of ultrasonic mixing, the regions of very low pressure are formed by the rapid oscillation of the probe. The vapor pockets, or bubbles, quickly expand and contract, thereby providing effective mixing of the components of the sample. Once the ultrasonic mixing of the sample is complete, the probe is removed from the sample, cleaned, and may then be used to mix another sample.

This process has significant drawbacks, however. First, the probe will often erode due to repeated contact with the material samples to an extent such that particles of the metal out of which the probe is formed, typically titanium, will contaminate the sample. Such contamination is often significant enough to affect the results of subsequent analysis of the sample. It is of great importance to maintain the purity of the samples so that the results of the analysis will be accurate.

Second, probes which do erode as a result of direct contact with many liquid samples over time need to be replaced regularly. Ultrasonic probes are precision parts which are not inexpensive. Therefore, frequent replacement of the probes is to be avoided if possible.

Third, the ultrasonic probes must be thoroughly cleaned between each sample mixing so as to avoid contamination of a subsequent sample by material from an earlier sample. It significantly increases the amount of time required to process multiple samples in series when the probe must be cleaned before each use. Thus, in automated systems for mixing many samples in series, the process can be extremely time-consuming.

What is needed then, is a system and method for utilizing ultrasonic mixing which minimizes the above-described drawbacks of traditional ultrasonic mixing.

SUMMARY OF THE INVENTION

It is an object of the present invention to provide a system and method for ultrasonic sample preparation which avoids contamination of the sample due to the erosion of the probe.

It is another object of the present invention to provide a system and method for ultrasonic sample preparation which minimizes the frequency with which probes must be replaced due to erosion.

It is still another object of the present invention to provide a system and method for ultrasonic sample preparation which obviates the need to clean the probe after each use on a sample.

These and other objects of the present invention are achieved by provision of a system for ultrasonic sample preparation including a sample container having a wall defining an outer surface and an inner volume for containing a sample material, a converter which converts AC electricity to mechanical vibrations in the ultrasonic range, and an ultrasonic probe in contact with the outer surface of the sample container. The ultrasonic probe is in communication with the converter and transmits the mechanical vibrations in the ultrasonic range to the wall of the sample container and thereby to the inner volume, thereby mixing the sample material.

In some embodiments, the outer surface of the sample container has a size and a shape, and the ultrasonic probe has a face having a size and shape corresponding to the size and shape of the outer surface so that the ultrasonic probe and the sample container are in intimate contact over substantially the entire face of the probe. In certain of these embodiments, the outer surface of the sample container defines a convex curve, and the face of the ultrasonic probe defines a concave curve having a size and shape complementary to a size and shape of the convex curve defined by the outer surface of the sample container. In certain embodiments, the sample container is generally cylindrical and the outer surface of the sample container has a radius of curvature, and the concave curve of the face of the ultrasonic probe has a radius of curvature substantially the same as the radius of curvature of the outer surface of the sample container.

In some embodiments, the sample container is generally cylindrical and has a volume of between about 1 mL and about 25 mL. In certain of these embodiments, the volume of the sample container is about 5 mL. In some embodiments, the sample container is formed from a polymeric material.

In some embodiments, the ultrasonic probe has a generally circular cross-section traverse to its length. In other embodiments, the ultrasonic probe has a generally rectangular cross-section traverse to its length. In some embodiments, the ultrasonic probe has a generally planar face. In some embodiments, the mechanical vibrations in the ultrasonic range have a frequency falling in a range from about 20 kHz to about 40 kHz.

In accordance with another aspect of the present invention, a method for sample preparation includes the steps of: (i) disposing a sample material in a sample container; (ii) placing the sample container on a mixing holder; (iii) moving an ultrasonic probe into contact with an outside surface of the sample container; and (iv) imparting ultrasonic mechanical vibrations to the ultrasonic probe via a converter and an electrical power source, thereby causing the ultrasonic probe to vibrate, which in turn causes a wall of the sample container to vibrate, thereby causing cavitation of the sample material in the sample container.

In some embodiments, the disposing step comprises the step of disposing a sample to be analyzed in the sample container, and adding a reagent thereto in the sample container. In some embodiments, the ultrasonic probe is prevented from directly contacting the sample material.

The invention and its particular features and advantages will become more apparent from the following detailed description considered with reference to the accompanying drawings.

DETAILED DESCRIPTION OF AN EMBODIMENT OF THE INVENTION

Figure 1:
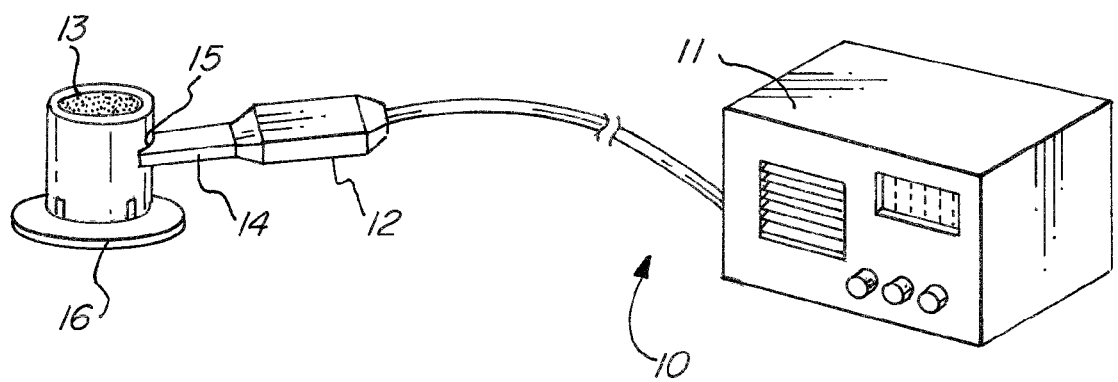
FIG. 1 is a perspective view of a system for ultrasonic sample preparation in accordance with an exemplary embodiment of the present invention.

Referring first to FIG. 1, a system 10 for the ultrasonic preparation of material samples according to one exemplary embodiment of the present invention is shown. The system 10 includes a converter 11 which converts electrical power from an electrical power source to ultrasonic energy. An ultrasonic probe 12 is coupled to the converter 11 and has a probe portion 14 which is vibrated in the ultrasonic range, such as, for example, in the frequency range from about 20 kHz to about 40 kHz.

Since ultrasonic sample preparation is well known, the operation and configuration of converter and probe 12 is not discussed in detail herein. However, as discussed above, it has been well-known to insert a probe, generally made of a metal such as titanium, into a sample vessel containing the material sample and then vibrating the probe at an ultrasonic frequency. In the present invention, on the other hand, probe portion 14 is not inserted into the sample vessel and does not come into contact with the material sample at all.

Instead, the probe portion 14 has a curved region 15 which makes intimate contact with a sample container 13. To use the system, a material sample is placed into the container 13 and then the container 13 is placed in a mixing holder 16. The probe 12 is brought into position against the container 13 and the converter is switched on. Ultrasonic energy is transmitted via the probe 12 to the container 13.

The sample container 13 may have any of multiple configurations, and may be made of numerous materials. When a sample container 13 having a rounded configuration is employed, as shown in FIG. 1, a probe portion 14 having a concave curved region 15 may be desirable. Even more desirable is of the radius of curvature of the curved region 15 closely matches the radius of curvature of the outer surface of the sample container 13, so that the probe portion 14 and curved region 15 are in close intimate contact and substantially the entire surface defining the curved region 15 is in contact with the outer surface of the sample container 13.

The sample container 13 may be made of, for example, a polymeric material, and may have any of numerous sizes. Typically, the sample container may have a volume in the range of 1 ml to 25 ml, with 5 ml producing advantageous results. In particular, 5 ml generally cylindrical polymeric tubes have been found to produce excellent results.

The system 10 may be used in conjunction with a method for sample preparation. This may be accomplished by disposing a sample to be analyzed in a sample container 13, and adding a reagent thereto in the sample container 13. The sample container may then be placed on a mixing holder 16, and an ultrasonic probe 12 moved into intimate contact with an outside surface of the sample container 13. The ultrasonic probe 12 may then be provided with ultrasonic energy via a converter 11 and an electrical power source. This ultrasonic energy causes a portion 15 of the probe 12 to vibrate, which in turn causes the walls of the sample container 13 to vibrate, thereby causing cavitation of the sample in the sample container 13. All of this is accomplished without the probe 12 ever coming in direct contact with the sample and/or reagent disposed within the sample container 13.

Figure 2:
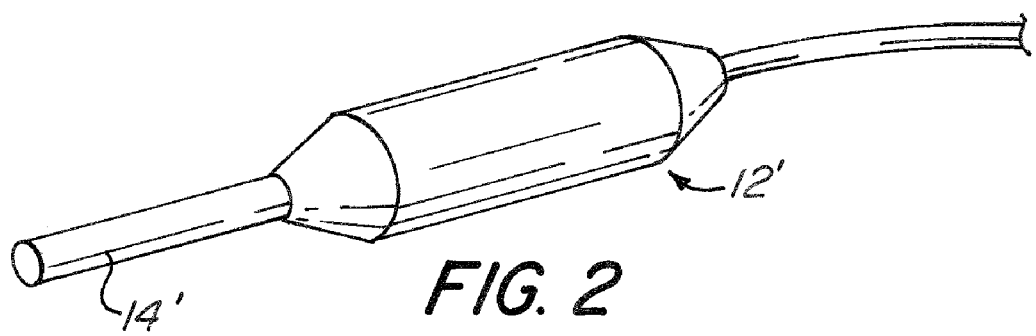
FIG. 2 is a perspective view of a cylindrical ultrasonic probe useable in connection with the system of FIG. 1.

FIG. 2 shows an alternative probe 12' having a cylindrical probe portion 14'. In a preferred embodiment, the cylindrical probe portion 14' has a diameter of at least ¼ of an inch. Smaller probes may melt or otherwise damage the sample container which would render it useless and/or contaminate the sample contained therein. Larger probes are generally preferred for all of the probe configurations described herein so that excessive localized heating may be avoided.

Figure 3:
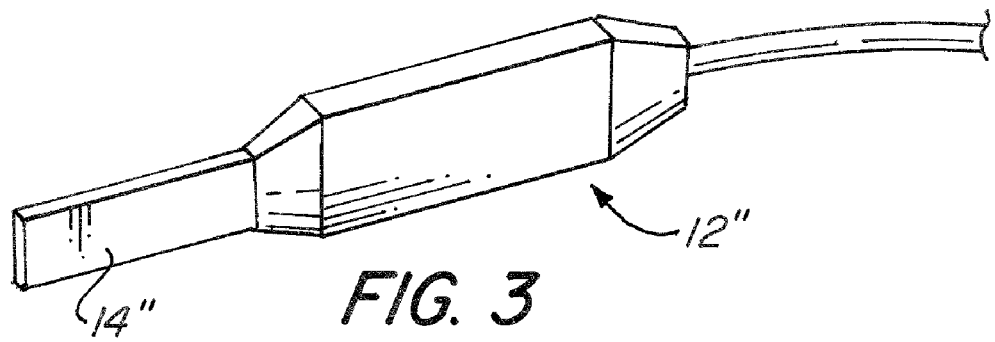
FIG. 3 is a perspective view of a flat rectangular ultrasonic probe useable in connection with the system of FIG. 1.

FIG. 3 shows a second alternative probe 12" having a flat, rectangularly shaped probe portion 14". This flat shape of the probe portion 14" allows for more substantial and intimate contact between the probe and the sample container 13. Such intimate contact allows for more efficient transmission of ultrasonic energy to the sample container 13.

Figure 4:
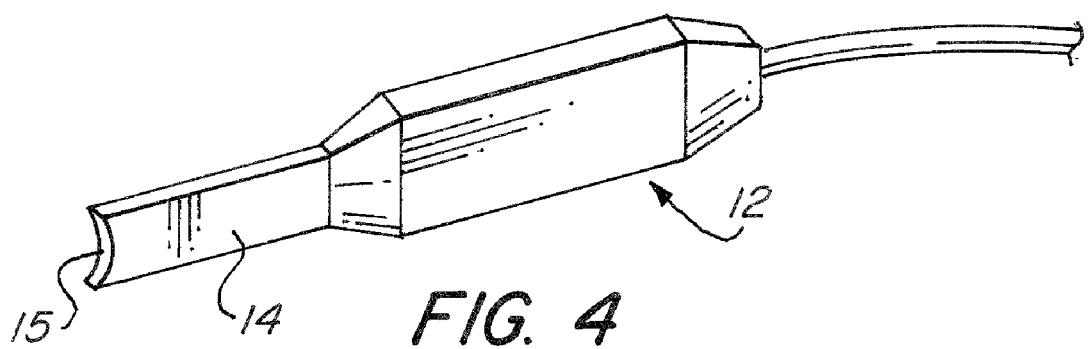
FIG. 4 is a perspective view of a specially shaped ultrasonic probe useable in connection with the system of FIG. 1.

FIG. 4 shows a close-up view of the probe 12 shown in FIG. 1. The probe 12 shown in FIG. 4 is shaped to match the configuration of a specific sample container. The probe 12 has a curved region 15 which is shaped to correspond to the outside surface of the sample container 13. Such an arrangement provides even more efficient transmission of ultrasonic energy to the sample container 13. A system utilizing this type of probe 12 is most advantageous when a standard-sized sample container is used for all samples to be processed by the system 10.

The present invention, therefore, provides a system and method for ultrasonic sample preparation which avoids contamination of the sample due to the erosion of the probe, which minimizes the frequency with which probes must be replaced due to erosion, and which obviates the need to clean the probe after each use on a sample.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for ultrasonic sample preparation comprising:
    a sample container having a wall defining an outer surface and an inner volume for containing a sample material, the outer surface of said sample container having a size and shape;
    a converter which converts AC electricity to mechanical vibrations in the ultrasonic range; and
    an ultrasonic probe, the ultrasonic probe having a size and a shape corresponding to the size and shape of the outer surface of the sample container, the ultrasonic probe having a face in direct contact with the outer surface of said sample container, so that said ultrasonic probe and said sample container are in intimate contact over substantially the entire face of the probe, said ultrasonic probe in communication with said converter and transmitting the mechanical vibrations in the ultrasonic range to the wall of the sample container and thereby to the inner volume, thereby mixing the sample material.

2. A system for ultrasonic sample preparation comprising:
a sample container having a wall defining an outer surface and an inner volume for containing a sample material;
a converter which converts AC electricity to mechanical vibrations in the ultrasonic range; and
an ultrasonic probe in contact with the outer surface of said sample container, said ultrasonic probe in communication with said converter and transmitting the mechanical vibrations in the ultrasonic range to the wall of the sample container and thereby to the inner volume, thereby mixing the sample material,
wherein the outer surface of said sample container has a size and a shape, and wherein said ultrasonic probe has a face having a size and shape corresponding to the size and shape of the outer surface so that said ultrasonic probe and said sample container are in intimate contact over substantially the entire face of the probe, and
wherein the outer surface of said sample container defines a convex curve, and wherein the face of said ultrasonic probe defines a concave curve having a size and shape complementary to a size and shape of the convex curve defined by the outer surface of said sample container.

3. The system of claim 1 wherein said sample container is generally cylindrical and has a volume of between about 1 mL and about 25 mL.

4. The system of claim 3 wherein the volume of said sample container is about 5 mL.

5. The system of claim 1 wherein said sample container is formed from a polymeric material.

6. The system of claim 1 wherein said ultrasonic probe has a generally circular cross-section traverse to its length.

7. The system of claim 1 wherein said ultrasonic probe has a generally rectangular cross-section traverse to its length.

8. The system of claim 1 wherein said ultrasonic probe has a generally planar face.

9. The system of claim 1 wherein the mechanical vibrations in the ultrasonic range have a frequency falling in a range from about 20 kHz to about 40 kHz.

10. A method for sample preparation comprising the steps of:
providing a sample container, the sample container having an outer surface with a size and a shape;
providing an ultrasonic probe having a face having a size and shape corresponding to the size and shape of the outer surface of said sample container;
disposing a sample material in the sample container;
placing the sample container on a mixing holder;
moving the face of the ultrasonic probe into direct contact with the outside surface of the sample container, so that the ultrasonic probe and said sample container are in intimate contact over substantially the entire face of the probe; and
imparting ultrasonic mechanical vibrations to the ultrasonic probe via a converter and an electrical power source, thereby causing the ultrasonic probe to vibrate, which in turn causes a wall of the sample container to vibrate, thereby causing cavitation of the sample material in the sample container.

11. The method of claim 10 wherein said disposing step comprises the step of disposing a sample to be analyzed in the sample container, and adding a reagent thereto in the sample container.

12. The method of claim 10 wherein the ultrasonic probe is prevented from directly contacting the sample material.

13. The system of claim 2 wherein said sample container is generally cylindrical and the outer surface of said sample container has a radius of curvature, and wherein the concave curve of the face of said ultrasonic probe has a radius of curvature substantially the same as the radius of curvature of the outer surface of the sample container.

* * * * *